(12) United States Patent
Krause et al.

(10) Patent No.: US 10,591,393 B2
(45) Date of Patent: Mar. 17, 2020

(54) METHOD OF PREPARING A SAMPLE FOR MICROSTRUCTURE DIAGNOSTICS, AND SAMPLE FOR MICROSTRUCTURE DIAGNOSTICS

(71) Applicant: Fraunhofer-Gesellschaft zur Förderung der angewandten Forschung e.V., München (DE)

(72) Inventors: Michael Krause, Halle (DE); Georg Schusser, Salzatal (DE); Thomas Höche, Halle (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 655 days.

(21) Appl. No.: 15/173,153

(22) Filed: Jun. 3, 2016

(65) Prior Publication Data
US 2016/0356683 A1 Dec. 8, 2016

(30) Foreign Application Priority Data

Jun. 5, 2015 (EP) .................................... 15170876

(51) Int. Cl.
*G01N 1/44* (2006.01)
*G01N 1/28* (2006.01)
(Continued)

(52) U.S. Cl.
CPC .............. *G01N 1/44* (2013.01); *G01N 1/286* (2013.01); *H01J 37/20* (2013.01); *H01J 37/31* (2013.01);
(Continued)

(58) Field of Classification Search
CPC ............ G01N 1/286; G01N 1/32; G01N 1/44; G01N 2001/2886; G01N 23/2204;
(Continued)

(56) References Cited

U.S. PATENT DOCUMENTS 5,270,552 A 12/1993 Ohnishi et al.
6,358,784 B1 * 3/2002 Zhang ................... B60R 25/066
257/E21.141
(Continued)

FOREIGN PATENT DOCUMENTS

CN 101241838 A 8/2008
CN 102023108 A 4/2011
(Continued)

OTHER PUBLICATIONS

S. Senz et al., "Optimisation of the wire-shadow TEM cross-section preparation technique", *Ultramicroscopy*, vol. 70, Dec. 1997, pp. 23-28 (Abstract only).

Primary Examiner — John Fitzgerald
Assistant Examiner — Truong D Phan
(74) *Attorney, Agent, or Firm* — DLA Piper LLP (US)

(57) ABSTRACT

A sample for microstructure diagnostics includes a sample body holder with accommodation structures to accommodate a sample body in a defined accommodation position; and at least one sample body produced separately from the sample body holder, the sample body having at least one solid handling portion and, adjoining the handling portion, a target portion thinner relative to the handling portion, the target portion being delimited at a narrow side by a sample body top side and, laterally, by side faces extending in a perpendicular or oblique manner in relation to the sample body top side, with the sample body being affixed to the accommodation structures in the accommodation position.

11 Claims, 5 Drawing Sheets

(51) Int. Cl.
*H01J 37/20* (2006.01)
*H01J 37/31* (2006.01)
*G01N 1/32* (2006.01)

(52) U.S. Cl.
CPC ....... *G01N 1/32* (2013.01); *G01N 2001/2886* (2013.01); *H01J 2237/2602* (2013.01); *H01J 2237/31745* (2013.01); *H01J 2237/31749* (2013.01)

(58) Field of Classification Search
CPC ..... H01J 2237/2602; H01J 2237/31745; H01J 2237/31749; H01J 37/20; H01J 37/31; B01L 3/505; B01L 3/508
USPC ........................................................ 73/864.91
See application file for complete search history.

(56) References Cited

U.S. PATENT DOCUMENTS

| | | | | |
|---|---|---|---|---|
| 2002/0166976 | A1* | 11/2002 | Sugaya | H01J 37/20 250/440.11 |
| 2006/0169917 | A1* | 8/2006 | Franz | H01J 49/04 250/441.11 |
| 2008/0032116 | A1* | 2/2008 | Hosoya | B01J 20/26 428/315.5 |
| 2008/0149822 | A1* | 6/2008 | Vertes | B82Y 20/00 250/282 |
| 2008/0258056 | A1* | 10/2008 | Zaykova-Feldman | G01N 23/04 250/307 |
| 2009/0103085 | A1* | 4/2009 | Hu | G01N 21/31 356/320 |
| 2009/0119807 | A1 | 5/2009 | Man et al. | |
| 2010/0176296 | A1 | 7/2010 | Kaito et al. | |
| 2012/0085903 | A1* | 4/2012 | Trimpin | H01J 49/044 250/282 |
| 2012/0175515 | A1* | 7/2012 | Hori | G01N 27/622 250/282 |
| 2013/0251914 | A1 | 9/2013 | Man et al. | |
| 2014/0054067 | A1* | 2/2014 | Heikenfeld | H01Q 15/0066 174/250 |
| 2016/0102248 | A1* | 4/2016 | Kanatzidis | H01L 31/032 250/458.1 |
| 2016/0141166 | A1* | 5/2016 | Toriumi | H01J 49/0418 250/288 |

FOREIGN PATENT DOCUMENTS

| | | |
|---|---|---|
| DE | 10 2004 001 173 A1 | 8/2005 |
| DE | 10 2011 111 190 A1 | 2/2013 |
| EP | 2 787 338 A1 | 10/2014 |

* cited by examiner

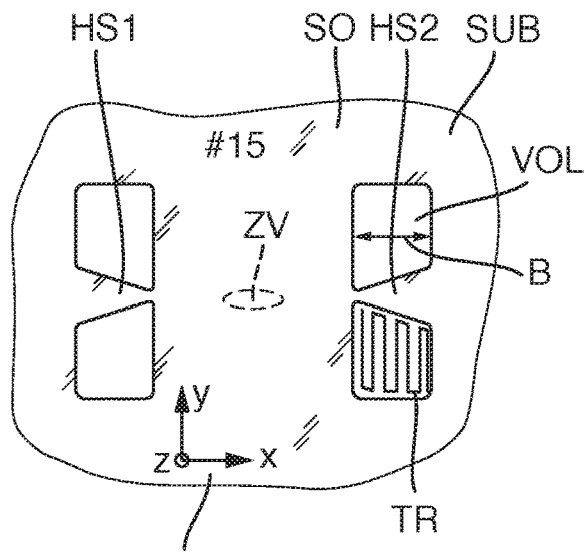
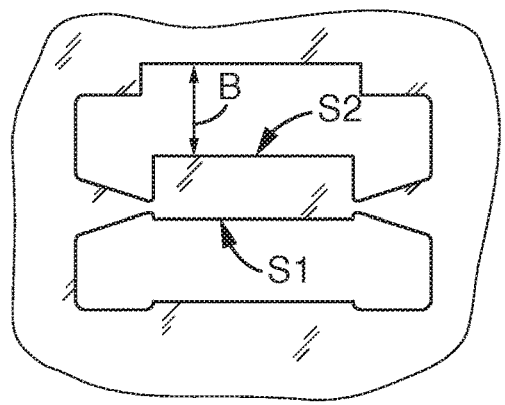
Fig. 1A                     Fig. 1B
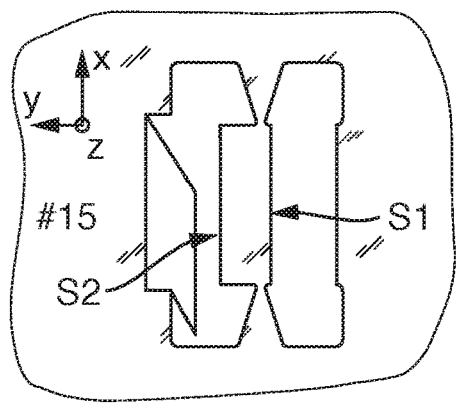
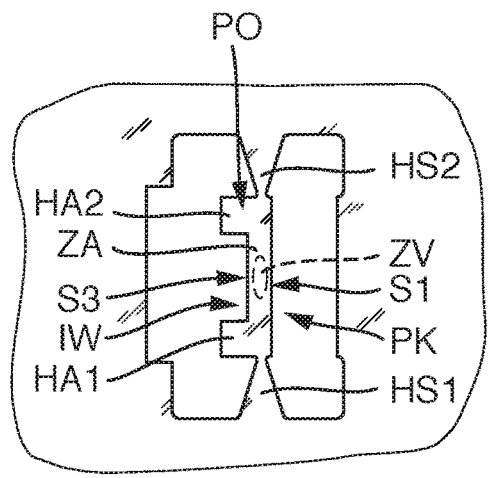
Fig. 1C                     Fig. 1D
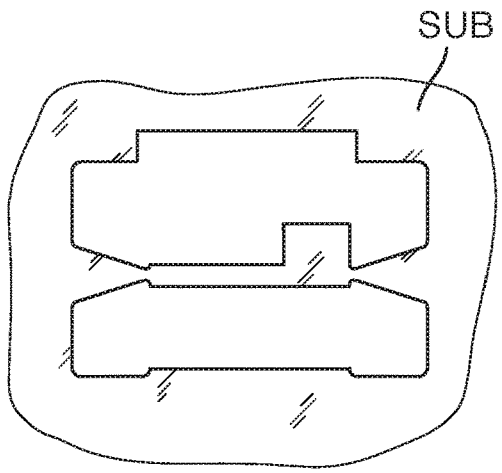
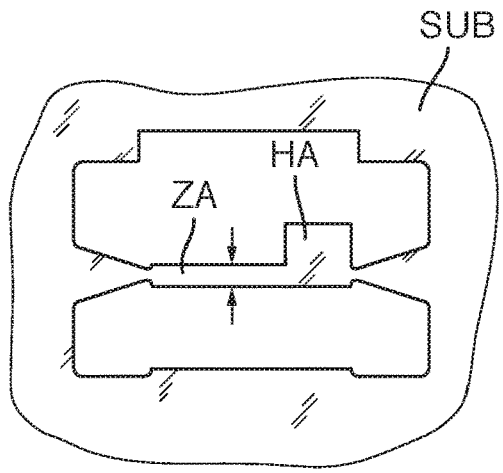
Fig. 1E                     Fig. 1F

METHOD OF PREPARING A SAMPLE FOR MICROSTRUCTURE DIAGNOSTICS, AND SAMPLE FOR MICROSTRUCTURE DIAGNOSTICS

TECHNICAL FIELD

This disclosure relates to a method of preparing a sample for microstructure diagnostics, wherein a sample body with a predeterminable form is prepared from a substrate by way of material-ablating laser beam processing and subsequently a target portion of the sample body is further processed by way of laser beam processing and/or ion beam processing to expose a target volume suitable for a microstructure examination. The disclosure also relates to a sample for microstructure diagnostics, which sample is prepared or can be obtained by the method.

BACKGROUND

Since its introduction in the 1930s, transmission electron microscopy (TEM) has found broad application in various different branches of science and economics. Due to the significantly improved resolution capability compared to light microscopy, the microstructure and nanostructure of various different preparations can be examined in great detail.

Atom-probe tomography (LEAP) is also used for chemical characterizations on the smallest length scales. This method for microstructure diagnostics enables a two-dimensional image and, moreover, supplies three-dimensional maps of the local composition with atomic resolution.

With increasing capability of the methods for microstructure diagnostics, the question regarding efficient and low-damage methods for preparing samples for these methods increasingly arises.

The problem of preparing cross-sectional samples often arises in the field of semiconductor technology and thin-layer technology, but also in other fields of technology. In contrast to a volume sample, a cross-sectional sample is a sample intended to serve for undertaking microstructure examinations in the region of interfaces between different materials adjoining one another in the region of an interface, e.g. in components with a layer structure.

Substantially two routes are followed to generate electron-transparent cross-sectional preparations, namely (i) the use of focused ion beam (FIB) systems to generate samples directly from the surface of a substrate by focusing ion beam technology and (ii) production of samples on the basis of sandwich bondings subsequently finished mechanically and then finally thinned by an Ar wide beam.

Within the last decade, preparation of cross-sectional samples for transmission electron microscopy in the form of FIB lamellas has found wide use in virtually all fields of microstructure analysis due to its great target accuracy. In the field of metrology and structure elucidation in highly integrated semiconductor components, it is currently considered to be de facto the only practically applicable method due to the achievable target accuracy (a few 10 nm).

However, fundamental physical restrictions lead to the high processing precision being accompanied by a low ablation rate. It is for this reason that only very small sample bodies with dimensions in the region of a few tens of micrometers can be prepared by FIB technology. Therefore, FIB generated sample bodies are mounted on carrier structures compatible with standardized sample holders of TEM installations, for the subsequent TEM analysis. For the purposes of the transfer, use is made of ex situ and in situ lift out techniques using micro- and nano-manipulators.

It is disadvantageous in that procedure that (i) the FIB installation is re-functioned from a precise processing tool to an expensive handling tool under vacuum conditions, as result of which the instrument capacity for processing is reduced, (ii) high additional costs are required for manipulator systems with sufficient precision in addition to the high acquisition costs of the actual FIB installation, (iii) there is a certain amount of risk that the susceptibility to errors of the overall system is increased by the complexity of the micro- and nano-manipulators, and (iv) the complexity of the overall workflow requires very well educated and experienced operators.

Methods for sample preparation operating with a combination of laser beam processing and ion beam processing have already been proposed as well. A sample body with a predeterminable form is prepared from a substrate by way of material-ablating laser beam processing and, subsequently, a target portion of the sample body is further processed by way of laser beam processing and/or ion beam processing to expose a target volume suitable for a microstructure examination. Those methods do not have the weakness of low ablation rates from FIB micro-processing arising as a matter of principle.

DE 10 2011 111 190 A1 describes a method of preparing a sample for microstructure diagnostics in which a flat disk is irradiated along two opposite surfaces thereof by a high-energy beam such that a recess extending approximately parallel to a central disk plane is introduced by radiation-induced material ablation into the two surfaces, with the two recesses extending on both sides of the central disk plane being introduced such that the longitudinal axes thereof, when seen in a projection of the longitudinal axes on this central disk plane, intersect at a predetermined finite angle and that, as seen perpendicular to the central disk plane, a material portion with a predefined minimum thickness, which is preferably already transparent to an electron beam, remains in the region of intersection of the two recesses and between the recesses as a sample. After the laser processing, the region of a low thickness can be thinned further by ion beam etching.

EP 2 787 338 A1 describes a method of preparing a sample for microstructure diagnostics in which a base structure consisting of the substrate material is isolated from a flat substrate radiating-in a laser beam in a manner perpendicular and/or oblique to the substrate surface, the base structure comprising a carrier structure and, integrally therewith, a structure carried by the carrier structure. By way of example, the carrier structure can have a C-shaped design, while the carried structure can be a thin bar-shaped target portion between the ends of the C-shaped carrier structure. The thickness of the target portion—as measured perpendicular to the substrate surface—corresponds to the substrate thickness. The side faces of the target portion extend parallel to the substrate surface. The target volume of interest lies in the target portion and it is isolated by further laser beam processing and subsequent ion beam processing after removing the base structure from the residual substrate and subsequently clamping the removed base structure into a clamp mounting. During laser beam processing, the laser beam is radiated-in in parallel or at an acute angle with respect to the side faces of the plate-shaped target portion such that e.g. electron-transparent regions arise, which can be transilluminated perpendicular to the former substrate surface.

The two methods are very well suited for quick and reliable preparation of volume materials. It is likewise possible to realize cross-sectional preparations by appropriate finishing of the initial material (e.g. sandwich bonding and subsequent mechanical comminution by sawing or grinding). However, there is increased outlay in terms of time. Moreover, experience of the user is required for good target accuracy.

It could therefore be helpful to provide a minimally invasive, reproducibly reliable, quick method with few artifacts for the targeted preparation of samples for microstructure diagnostics, suited equally to cross-sectional samples and volume samples and to prepare samples of the highest quality for cross-sectional transmission electron microscopy (X-TEM) within a relatively short period of time.

SUMMARY

We provide a method of preparing a sample for microstructure diagnostics, wherein a sample body with a predeterminable form is prepared from a substrate by way of material-ablating laser beam processing and subsequently a target portion of the sample body is further processed by laser beam processing and/or ion beam processing to expose a target volume suitable for a microstructure examination, including:

(a) releasing the sample body from the substrate by at least one laser processing operation by radiating-in at least one laser beam in a manner perpendicular and/or oblique to a substrate surface such that a sample body arises, the sample body being delimited at a sample body top side by a region of the substrate surface and, laterally, by side faces oriented in an oblique or perpendicular manner in relation to the substrate surface, wherein a form of the sample body is generated, which form has at least one solid handling portion and, adjoining the handling portion, a target portion thinner relative to the handling portion, the target portion being delimited at a narrow side by the sample body top side and, laterally, by side faces extending in a perpendicular or oblique manner in relation to the sample body top side;

(b) producing a sample body holder separate from the sample body and having accommodation structures adapted to the form of the sample body for the purposes of accommodating the sample body in a defined accommodation position;

(c) removing the sample body that was released from the substrate;

(d) affixing the sample body removed from the substrate to the accommodation structures of the sample body holder;

(e) carrying out at least one further material-ablating processing step of at least one side face of the sample body in the region of the target portion by laser beam processing and/or ion beam processing to expose the target volume.

We also provide a sample for microstructure diagnostics including a sample body holder with accommodation structures to accommodate a sample body in a defined accommodation position; and at least one sample body produced separately from the sample body holder, the sample body having at least one solid handling portion and, adjoining the handling portion, a target portion which is thinner relative to the handling portion, the target portion being delimited at a narrow side by a sample body top side and, laterally, by side faces extending in a perpendicular or oblique manner in relation to the sample body top side, with the sample body being affixed to the accommodation structures in the accommodation position.

BRIEF DESCRIPTION OF THE DRAWINGS

FIG. 1 shows, in partial FIGS. 1A to 1F, various phases when isolating a sample body from a substrate in one example.

DETAILED DESCRIPTION

Figure 2:
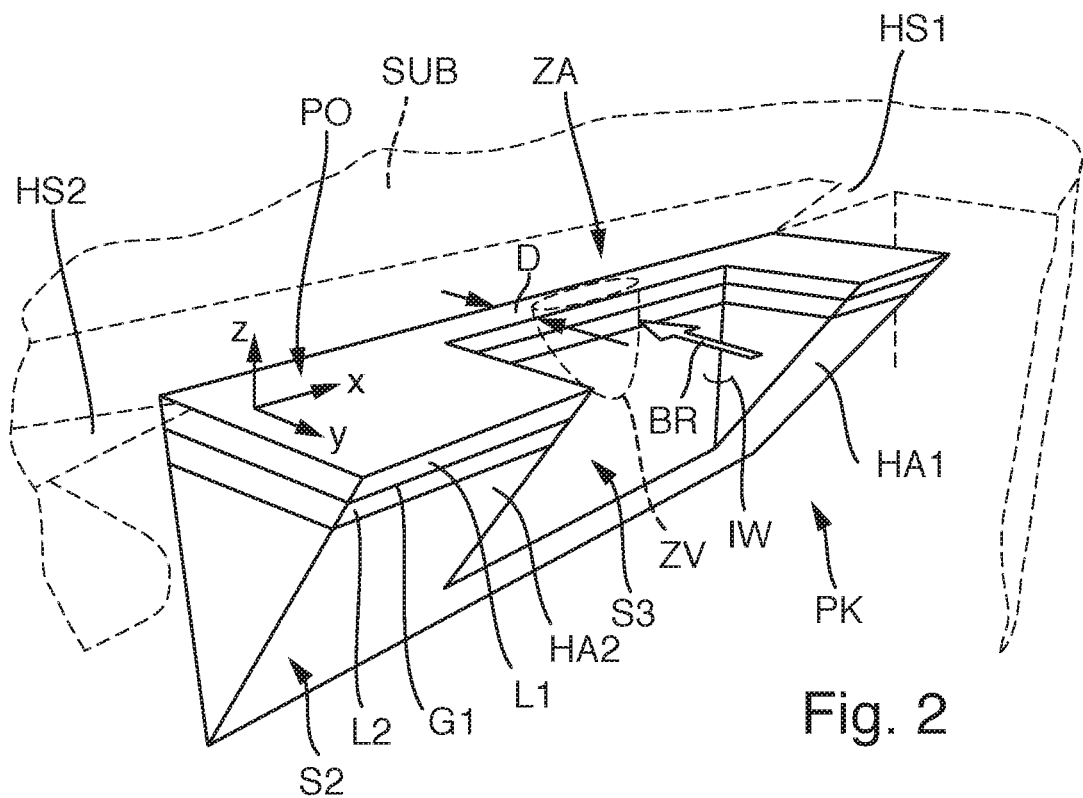
FIG. 2 shows an oblique perspective view of a sample body.

The method of preparing a sample for microstructure diagnostics is a multi-stage method in which in an earlier stage, a sample body with a predeterminable form is prepared from a substrate by way of material-ablating laser beam processing and in which, subsequently, a target portion of the sample body is further processed by way of laser beam processing and/or ion beam processing to expose a target volume intended to be suitable for a microstructure examination with the aid of one or more methods of microstructure diagnostics. The target volume is that spatially restricted region of the sample body in which the microstructure is intended to be examined in more detail. The term "sample" denotes that unit intended to be installed into a corresponding sample accommodation system in an installation for microstructure diagnostics, for example, into a sample accommodation system of a transmission electron microscope.

In step (a), the sample body is released by at least one laser processing operation by radiating-in at least one laser beam in a manner perpendicular and/or oblique to the substrate surface. The method is conducted such that a sample body arises which is delimited at a sample body top side by a region of the substrate surface. At the sides at an angle to the sample body top side, the sample body is delimited by side faces oriented in an oblique or perpendicular manner in relation to the substrate surface. These are exposed or generated for the first time by the laser processing operation.

During the release step, a form of the sample body is generated, which form has at least one solid handling portion and, adjoining the handling portion, a target portion thinner relative to the handling portion. The target portion is delimited at a narrow side by the sample body top side and, laterally, by the side faces extending in a perpendicular or oblique manner in relation to the sample body top side. The position of the target portion is selected such that the target volume of interest lies within the target portion.

The geometric form and dimensions of the handling portion and the target portion are controlled for their respective functions. The handling portion should be solid and mechanically stable such that handling of the sample body can take place in the subsequent method steps with the aid of the handling portion without contacting the target portion being necessary. In this respect, the handling portion has the function of a handle portion, which a user can subsequently contact manually with the aid of an instrument such as e.g. forceps or else with the aid of a manipulation system to handle the sample body in subsequent method steps.

The thinner target section need not have particularly high mechanical stability. Therefore, the relevant thickness thereof can be set such that, during the subsequent material-ablating preparation steps to expose the target volume, only relatively little material still needs to be ablated, as result of which only relatively little time is required by the subsequent material-ablating method steps. The form of the target portion can be adapted to the requirements of the envisaged microstructure diagnostic method. By way of example, the target portion can have a substantially plate-shaped design, although this is not necessary. The target portion can also have the form of a plate stepped on one or both sides and/or a form with at least one polygonal end face, i.e. an end face which has two or more surface portions at an oblique angle with respect to one another.

A sample body holder separate from the sample body is produced in a manner spatially and temporally independent of releasing the sample body. The sample body holder has accommodation structures adapted to the form of the sample body and accommodating the sample body in a defined accommodation position on the sample body holder. The sample body holder can be produced prior to the release step and it can be completely finished before the sample body is generated. Sample body holders can be manufactured for storage. It is also possible for the release step to overlap in time with the production of the sample body holder or to be carried out, in terms of time, completely after releasing the sample body.

The accommodation structures on the sample body holder are adapted in terms of, inter alia, the geometry thereof to the form of the sample body or to the form of a specific class of sample bodies such that a sample body holder is generally not a universal holder but may be controlled in view of certain sample body geometries. Away from the accommodation structures, the sample body holder can, in principle, have a free design, in particular such that it fits to accommodation structures in devices for subsequent method steps and for the actual microstructure examination.

The released sample body is removed from the substrate at a suitable time within the scope of step (c) (removal step).

Thereupon, the removed sample body is affixed to the accommodation structures of the assigned sample body holder in step (d) such that it is situated in the desired accommodation position predetermined by the form of the accommodation structures. As a result of the affixing step (d), a fixed spatial relationship arises between sample body and sample body holder. As a result of the fixation, the connection also holds in movements or vibrations and/or in different orientations.

The sample body holder and the sample body affixed thereon are the constituent components of the sample, the form and dimensions of which are adapted to the form and dimensions of a sample accommodation system in an installation for microstructure diagnostics. Hence, a multi-part sample is developed, for example, a two-part sample made of sample body holder and sample body affixed thereon.

In some method variants, the sample body is fastened or affixed to the accommodation structures by adhesion with the aid of an adhesive. Other method variants make do without the use of auxiliary means by virtue of the sample body being fastened or affixed to the accommodation structures by clamping, i.e. in a purely mechanical manner by frictional engagement. Depending on the materials of sample body and sample body holder, welding is also possible, e.g. by a laser beam. It is also possible for an interlocking connection to be established by e.g. latching between sample body and accommodation structures.

After producing the sample by affixing the sample body onto the sample body holder, at least one further material-ablating processing step is carried out in step (e) at at least one side face of the sample body in the region of the target portion to expose the target volume. For this final processing step or for these final processing steps (one step or a plurality of steps), use can be made of laser beam processing and ion beam processing, either as an alternative to one another or in combination with one another. Often times, further processing is initially carried out by laser beam processing, almost until the ultimately desired form is reached, and this will be followed by ion beam processing to dispose of processing remains of the laser beam processing and finally expose the target volume to the subsequent microstructure examination.

The method and samples produced with the aid of the method offer numerous advantages compared to known methods.

(i) The former substrate surface in the region of the sample body surface can remain largely untouched during the whole sample preparation. Therefore, when necessary, the target volume can lie in the direct vicinity of the former substrate surface (sample body surface). As result, an option for direct preparation of cross-sectional samples without sandwich bonding of the initial material is provided.

(ii) The observation direction in a subsequent microstructure examination can lie parallel or approximately parallel to the former substrate surface, as a result of which, inter alia, interfaces between layers close to the surface become observable.

(iii) The thickness of the target portion can be set independently of the substrate thickness. Hence, there is a loss of restrictions in respect of the maximum substrate thickness which exist in some conventional methods.

(iv) The target portion can already be very thin prior to the final processing operation in step (e) as the sample body nevertheless remains manipulatable at all times by way of the comparatively thicker, more solid handling portion. A thinner target portion shortens the subsequent thinning processes, as a result of which the finished sample is obtained more quickly.

(v) Furthermore, there is no need to use motor-driven micro-manipulators or nano-manipulators to manipulate the sample or the sample body. The solid handling portion can be designed independently of the target portion such that it can also be gripped and/or manipulated or accommodated by a user with tweezers or any other suitable gripper instrument.

(vi) The method permits a virtually artifact-free realization of samples with an electron-transparent target volume. Samples for other examination methods requiring the smallest sample dimensions and an accurate preparation are also possible.

(vii) Moreover, the separate production of combinations, adapted to one another, of sample bodies and sample body holders offers the potential to increase the throughput of the sample preparation compared to conventional methods.

In some cases, it is sufficient for a sample body to have only a single handling portion. In other instances, a first handling portion and at least one second handling portion, spaced apart from one another, are generated at the sample body. A comparatively thinner intermediate portion can lie between the handling portions. Two (or more) handling portions offer more options for contact on the sample body during the subsequent method steps. Moreover, with the aid of two spaced apart handling portions, it is possible to achieve a particularly positionally accurate and loadable fixation at appropriately designed accommodation structures of a sample body holder with a multiplicity of contact faces.

A mechanically stable handling portion can be attached to one end of the sample body. It is also possible to embody a handling portion approximately in the center and/or at a distance from both ends of a sample body. It can have a defined thickness dimensioned such that it can be inserted in a largely interlocking manner between two webs or guides of an accommodation structure and then affixed. If two handling portions are provided, these can be e.g. attached to the opposite ends of the sample body such that the latter can be similar to a bone. However, the mechanically stable, thicker handling portions need not lie on that lateral edge of the sample body, but can also be offset inwardly from the edge. Three or more handling portions separated from one another by intermediate portions may be expedient for reasons of stability in e.g. very long sample bodies.

The intermediate portion lying between the first handling portion and the second handling portion can be a portion of the sample body which is not required as target portion and which may predominantly serve for better fixation at the accommodation structures. In other instances, the target portion lies between the first handling portion and the second handling portion such that the intermediate portion corresponds to the target portion. As a result, a particularly accurate fixation of the sample body in terms of position and secure positioning of the target portion at the sample body holder can be promoted.

In release step (a), the sample body can be completely released within the scope of a continuous laser processing operation such that it can readily be removed from the substrate. In other instances, the procedure undertaken in release step (a) is such that a holding structure made of substrate material remains at at least one point of a side face of the handling portion, the holding structure connecting the otherwise released sample body in the region of the handling portion with an adjoining portion of the substrate such that the sample body is only connected to the remainder of the substrate by way of the holding structure. What this can achieve is that the otherwise released sample body is initially only held by the residual substrate in subsequent operations such that no separate holding apparatuses are necessary. The released sample body can remain connected to the substrate up until the removal of the sample body (step (c)).

In the context of removing the sample body, there are a number of options to release the connection between the (largely) released sample body and the substrate. In some method variants, the removal of the sample body in step (c) immediately causes a separation of the connection between the sample body and the substrate in the region of the holding structure. By way of example, the holding structure can be broken up by the act of removal without further measures or means being required for detachment.

If a plurality of handling portions and/or a plurality of holding structures are present, there can also be a procedure to the extent that one or more holding structures are disposed of by the laser beam processing such that the sample body then becomes free. In principle, the method can be carried out such that all holding structures are removed by laser irradiation. By way of example, it is possible to separate a holding structure by a laser beam immediately prior to the removal, optionally without simultaneous blowing-on with pressurized air. In these cases, it is generally expedient to contact the sample body prior to dissolution of the holding structures such that the subsequent removal can be undertaken quickly and easily. In principle, it is also possible for the sample body initially to fall from the substrate after dissolution of a final holding structure and for it to be subsequently accommodated.

Release step (a) can be carried out in different ways. In some method variants, a volume region made of substrate material is disposed of adjacent to at least one of the side faces during the laser beam processing within the scope of release step (a), which volume region—measured perpendicular to the normal of the released side face—has a width at one of the plurality of positions or over the whole length which is a multiple of the width of a laser beam cutting path. Thus, a large-scale release is carried out in the region of the respective side face. As a result, relatively large (when compared to the width of a laser beam cutting path), material-free volume regions can arise adjacent to a side face, which volume regions promote effective cleaning of the processing zone during the laser processing by way of being blown thereon or being blown free and which volume regions may also contribute to improved handling during the detachment because the accessibility to the sample body is improved. Moreover, we found that large-scale exposed side faces can have a substantially better surface quality than flank faces of a simple cut gap or of a laser beam cutting path.

While a laser beam cut width typically is approximately 10 µm to 30 µm, depending on focusing and material, the aforementioned width of the volume region preferably is 200 µm or more, for example, 300 µm to 400 µm.

The large-scale release with the generation of relatively large material-free volume regions can e.g. be achieved by a scanning guidance of a focused laser beam by virtue of the region to be exposed being scanned in succession by mutually parallel cuts or partly overlapping cutting paths of a focused laser beam.

Non-scanning method variants are also possible, in which suitable beam shaping can obtain the disposal of a relatively large volume region adjacent to a side face to be exposed. By way of example, a method of mask projection can be used when releasing the sample body to dispose of relatively large volume regions of substrate material simultaneously by way of large-area irradiation with laser radiation. Beam shaping to obtain a specific beam cross section can also be obtained with the aid of diffractive optical elements or other apparatuses of the laser processing system that serve for beam shaping. It is also possible to use lasers, e.g. solid-state lasers that generate a line focus per se.

The method places no particular requirements on the thickness of the substrate from which the sample body should be isolated. To the extent that the substrate is thin enough, it may be sufficient when releasing the sample body to cut the sample body out of the substrate when generating the side surfaces such that substrate surface lying opposite the sample body top side forms a rear side interface of the sample body. Depending on the substrate material, this is expedient in many cases, e.g. in substrate thicknesses up to approximately 500 μm to at most 650 μm.

However, it is readily also possible to isolate a sample body from a region of a thick substrate close to the surface without completely separating the substrate. In one method variant, the sample body is generated in such a way during the release step (a) that an extent of the sample body measured perpendicular to the substrate surface is less than a thickness of the substrate measured perpendicular to the substrate surface. In particular, it is possible to proceed such that two side faces angled in relation to one another and lying opposite one another are generated in an intermediate step by laser beam processing, within the scope of release step (a), which side faces intersect at a line of intersection lying in the interior of the substrate. By way of example, the angle can be less than 90°. Hence, the sample body can be released from the region close to the surface from at least one side by way of oblique incidence of laser radiation. The sample body top side can be undercut at at least one side. It is also possible to generate an undercut at two opposing sides. By way of example, the angles of incidence measured relative to the surface normal of the sample body top side can be approximately 10° to approximately 55°. However, often no more than 45° are provided and also sufficient. Hence, after this processing stage, the sample body, when viewed from a suitable direction, can have approximately the form of a wedge which can have a design symmetrical with respect to a central plane or else asymmetrical. By way of example, one side face can extend perpendicular to the sample body top side, while another side face runs obliquely toward this side face. Oblique faces on both sides are also possible.

The sample body can be isolated from a substrate with uniform substrate material such that a volume sample arises. However, it is also possible for the substrate to have one or more layers or layer portions or layer segments separated by interfaces in the region of the substrate surface. A typical example for such substrates is structured semiconductor components. The layers can be continuous or laterally structured. At least one interface can extend substantially parallel to the substrate surface. Alternatively or additionally, there can be one or more interfaces extending obliquely or perpendicularly to the substrate surface. In any case, the sample body can be generated such that one or more interfaces are oriented substantially perpendicular to at least one side face of the target portion.

The phrase "substantially perpendicular" means that this interface extends perpendicularly or with an obtuse angle, for example, of less than 55° in relation to the surface normal. The phrase "substantially parallel" means that the interface extends parallel or with an acute angle, for example, of less than 45° in relation to the substrate surface. Thus, this lends itself to the option of preparing cross-sectional samples, as is already mentioned at the outset.

In the method, the form of the sample body can expediently be adapted to a corresponding design of fitting accommodation structures of the sample body holder. In many cases, a particularly reliable and positionally accurate fixation of the sample body on the sample body holder can be achieved by virtue of the sample body being designed such that an interior angle arises between the target portion or intermediate portion and an adjoining handling portion, with a side face of the target portion or intermediate portion and a side face of the handling portion intersecting at an angle, for example, at a right angle, at the interior angle. As a result, a defined stop for attachment to correspondingly designed accommodation structures of the sample body holder can be achieved. One interior angle may be sufficient, but provision is often made for two or more such interior angles.

The concept of the multi-part sample offers expedient design possibilities for the configuration of the sample body holder. In some instances, the sample body holder is manufactured from a holder material differing from the substrate material. Hence, there is freedom in respect of the material selection for the sample body holder which, for example, can be controlled, inter alia, for the holding function thereof, independently of the substrate material.

The holder material can be selected in accordance with one or more of the following criteria.

(i) The holder should have structural integrity for a reliable holding function, and so it may be advantageous to manufacture the sample body holder from a single piece of material, even if not mandatory.

(ii) First, production of the sample body holder should be cost effective. However, second, possibly complicated prescriptions in respect of the design of the sample holder, for example, in the region of the accommodation structures, must be observed. Therefore, production is carried out by laser beam processing from a plate or film of a suitable holder material in some instances. In these cases, laser processability with high precision should be possible.

(iii) To ensure the holding function in the further processing steps in accordance with step (e), the holder material should have a lower ion etching rate than the material of the associated sample body.

(iv) Furthermore, it may be expedient if the holder material has good electric conductivity and/or thermal conductivity.

(v) For some types of sample bodies and/or subsequent microstructure examination methods, it may be expedient to take care that the holder material constitutes a chemical complement to the sample body material so that subsequent chemical analyses are not impaired by background signals.

In view of one or more of these criteria, we found it to be advantageous in many cases if the holder material has a metal or is a metal. The term "metal" should comprise both pure metals and metallic alloys with two or more components. Currently, titanium is believed to be a particularly suitable material, which, first, is readily processable and, second, has lower etching rates during ion irradiation. Moreover, metallic materials can be isolated in very complex configurations from a film or plate, optionally also from a solid initial piece by laser beam processing. Preferably, the sample body holder is produced from a plate or film of the holder material by laser processing. A sample body holder can also be produced by a constructional technique, e.g. by 3D printing or by a MEMS process.

It is also possible for a sample body holder to consist partly or completely of a plastic, graphite or any other form of elemental carbon, or of a ceramic material such as e.g. $Al_2O_3$.

For the purposes of a positionally accurate fixation of the sample body to the sample body holder, we found it to be expedient in many instances for the accommodation structures to have one or more holding webs to affix the sample body with at least one abutment face to mount a corresponding side face of the sample body on a holding web. In particular, an exterior angle, for example, a right angle adapted to the aforementioned interior angle can be formed on a holding web. As a result, a defined area contact is possible between two faces at an angle to one another when fixing the sample body to the sample body holder. So, the position of the sample body in respect of the sample body holder is set in at least two mutually perpendicular directions. A further abutment face can be provided in a manner oblique or perpendicular thereto.

It appears expedient in many cases if the accommodation structures are generated such that they have one or more holding webs to affix the sample body with a holding web having a first web portion and a second web portion aligned at an angle to the first web portion. The aforementioned angle can preferably be a right angle. By way of example, the angle shape of a holding web can be an L-shape or a T-shape. Using three web portions at an angle to one another, accommodation structures in the form of eyes (rectangular eyes) are possible. Such forms offer exterior angles and interior angles suitable as abutment faces, in a plurality of directions. It is possible to form relatively small, defined contact zones between mutually adjacent, preferably plane face portions of the sample body and a holding web, which contact zones, in fixation by adhesive, ensure that adhesive remains only in the small area regions required for the adhesive function.

Many different adhesives are usable. An adhesive should cure relatively quickly but allow for a certain correction possibility during fixation, have sufficient viscosity for good wetting and be suitable for vacuum.

A target preparation of regions close to the surface can be difficult, particularly in relatively easily etchable sample body material. In some instances, these circumstances are accounted for by virtue of the accommodation structures designed such that they have or form a shadowing web adapted to the sample body top side, the shadowing web consisting of a material having a lower etching rate or ablation rate than the substrate material in ion irradiation and/or laser irradiation. As a result, the advantages of the "wire shadow" method, known per se, can be employed by a particular refinement of the accommodation structures without it being necessary to use separate shadowing elements such as e.g. a shadow wire. In respect of details about the known wire shadow technique, reference is made in an exemplary manner to "Optimisation of the wire-shadow TEM cross-section preparation technique" by S. Senz et al., in Ultramicroscopy 70 (1997), pages 23-28.

Alternatively or additionally, it is also possible, prior to affixing the sample body to the accommodation structures, to apply a sacrificial layer onto the sample body top side, at least in the region of the narrow side of the target portion, the sacrificial layer consisting of a material having a lower ablation rate (material ablation rate) or etching rate than the substrate material in laser irradiation and/or ion irradiation and which preferably also contributes to an improved thermal management by virtue of the sacrificial layer having better thermal conductivity than the substrate material.

Both a shadowing web and a sacrificial layer can cause the substrate material initially shadowed thereby from laser beams and/or ion beams to become ablated only once the protective material of the shadowing web or of the sacrificial layer is used up or ablated. If the laser irradiation and/or ion irradiation is terminated just before, upon or briefly after reaching this state, a target volume can remain immediately following the shadowing web or the sacrificial layer and it can be subsequently observed.

We also provide a multi-part sample for microstructure diagnostics, which can be, or was, produced by a method of the type described herein. The sample has a sample body holder with accommodation structures to accommodate a sample body in a defined accommodation position. Furthermore, the sample has at least one sample body produced separately from the sample body holder, the sample body having at least one solid handling portion and, adjoining the handling portion, a target portion thinner relative to the handling portion, the target portion delimited at a narrow side by a sample body top side and, laterally, by side faces extending in a perpendicular or oblique manner in relation to the sample body top side. The sample body is affixed to the accommodation structures in the accommodation position.

Further advantages emerge from the subsequent description of preferred examples explained below on the basis of the figures.

Below, various aspects of a method of producing a cross-sectional sample for transmission electron microscopy (TEM) are described in an exemplary manner on the basis of FIGS. 1 to 3. A sample body is isolated from a region of a substrate SUB selected in a targeted manner, the sample body subsequently being fastened in a sample body holder adapted thereto and intended to form a sample for microstructure diagnostics by TEM together with the sample body holder.

In FIGS. 1A to 1F, schematic FIG. 1 shows various phases of the isolation of a sample body from the substrate SUB. FIG. 2 shows an oblique perspective view of a sample body. FIG. 3 shows the sample body from FIG. 2 after affixing the sample body to a sample body holder adapted thereto.

In a top view, FIG. 1A shows a portion of the substrate surface SO of a substrate SUB from which a sample body is intended to be isolated, and the sample body containing a portion of the substrate surface. A substrate coordinate system SKS has been plotted for improved orientation. The target volume ZV, subsequently intended to be examined by TEM, immediately adjoins the substrate surface SO in the z-direction. In the example, the substrate surface is planar. It can also be curved. A pre-preparation of the substrate surface is generally not necessary. For example, it need not be polished. By way of example, the substrate can be a semiconductor component constructed from multiple layers.

A largely freely selectable sample volume is released from the surface-near region at a defined position by successive ablation of material by laser beam processing under both perpendicular and oblique incidence of a laser beam. To this end, regions with subsequent holding structures HS1, HS2 are generated first (FIG. 1A). Subsequently, the basic structure of the sample body PK to be removed is released under partly perpendicular, partly oblique incidence of the laser beam, with the sample body only connected to the remainder of the substrate in the region of the holding structures (FIGS. 1B and 1C). The sample body blank generated up until then only connects to the remainder of the substrate in the region of the holding structures.

In the subsequent processing phases, a central portion of the sample body blank is thinned by further material ablation, likewise by a focused laser beam such that a relatively narrow target portion ZA containing the target volume ZV arises. Structurally more solid or thicker portions, in the region of which the holding structures connect to the blank of the sample body, remain at both longitudinal ends of the target portion. These solid portions serve for subsequent handling of the sample body PK and are therefore denoted as handling portions HA1 HA2 (FIG. 1D). The sample body generated in this manner is therefore characterized by a low thickness in the region of the target volume, i.e. in the target portion, but also by mechanically particularly stable regions on the edge (handling portions).

The sample body is only held by the two holding structures HS1, HS2 adjoining the opposing handling portions during the whole laser processing, which holding structures taper in a wedge-shaped manner toward the sample body and form a predetermined breaking point at the transition to the thicker handling portions. By holding the sample body by the holding webs, it is possible during these phases of the processing to clean any processing remains (debris) of the laser processing by blowing the remains away with pressurized air or any other gas under pressure without the sample body being blown away thereby. The configuration shown in a plan view in FIG. 1D is also depicted in the oblique perspective view of FIG. 2.

Further processing steps can follow on the sample body held in the substrate by the holding structures. In particular, as shown in FIG. 1E, it is still possible to remove one of the solid handling portions by laser processing such that the resultant sample body has an L-shape and only a single solid handling portion and, adjoining the latter, a thin target portion, with one of the holding structures contacting the handling portion and the opposite holding structure contacting the target portion. The sample body generated thereby can then be thinned further in the region of the target portion by way of further laser processing (FIG. 1F).

The sample body micro-processed by laser in this manner can then be removed from the substrate in a further method step, for example, using conventional tweezers, e.g. reverse-action tweezers. A user would only contact the handling portion and would not touch the thinner target portion. The sample body can be broken from the residual substrate at the thinnest positions of the holding structures HS1, HS2 in the region of the predetermined breaking points and it is then free for further handling.

A laser processing device suitable for carrying out the aforementioned method steps has a laser, a galvanometer scanner and focusing optics to be able to generate a focused laser beam directed onto the substrate and guide the laser beam along previously programmable trajectories. It is also possible to use laser processing devices with other positioning units enabling a controllable relative movement between laser beam and substrate. The substrate from which the sample body is intended to be removed is accommodated in a workpiece receptacle. When necessary, the workpiece receptacle can be interchanged with a holder for post-processing. Furthermore, the workpiece receptacle can be tilted about an axis and rotated about an axis independent thereof to be able to set the angle of incidence and the direction of incidence of the laser beam in a freely programmable manner for each point of incidence. Moreover, the target position can be positioned exactly in the eucentric tilt axis of the workpiece receptacle by way of an xy-displacement of the substrate. The laser processing device is furthermore equipped with a fan system and a suction system. The fan system can be used to blow onto the region currently processed by the laser beam to carry away arising processing remains with the aid of the pressurized gas such that these cannot deposit on the processed remainder of the substrate. Using the suction system, the processing remains can be sucked away in an environmentally compatible manner. Furthermore, provision is made of an observation apparatus with a digital camera which can be used to target the respective target position with an accuracy of a few micrometers. Programming and operation is carried out by a software interface on an operating unit, also containing the central control of the laser processing device.

Within the scope of the laser processing, the sample body holder can be marked to be tracked within the scope of QM systems, for example, with the sample designation, continuous numbers or a matrix code or barcode.

The processing strategy depicted in an exemplary manner on the basis of FIGS. 1A to 1F uses these instrument-based possibilities within the meaning of a quick and sparing preparation of a sample body. Proceeding from the substrate SUB with an unbroken surface, the processing state shown in FIG. 1A is achieved by virtue of the focused laser beam being guided by the galvanometer scanner along a meandering trajectory TR (or by another scanning movement, e.g. linear advance) in the volume regions to be removed by laser beam processing such that approximately cuboid or polygonally delimited volume regions VOL are removed from the substrate material. The width B (measured perpendicular to the bounding side faces) of the volume regions corresponds to a multiple of the width of a laser beam cutting path. By way of example, the width B can be 200 µm to 400 µm. As result, large free spaces arise adjacent to the exposed side faces and these simplify cleaning by blowing-free and also offer simplified access to the sample body to be removed within the scope of subsequent handling. The large-scale exposure renders it possible to generate side faces with a very high surface quality. The processing strategy (e.g. by meandering, boxes, lines and the like) has a significant influence on the quality of the exposed side faces. The side faces are generally significantly smoother than flank faces of a laser cutting path.

In this phase, work is carried out with virtually perpendicular incidence of the laser beam, i.e. with a direction of incidence of the laser beam approximately parallel to the surface normal of the substrate (z-direction). If a side face perpendicular to the sample surface is intended to be generated by a focused laser beam, a slight counter-tilt (by a few degrees) is required in an envisaged fashion to compensate the flank angle.

Subsequently, the side faces lying opposite one another in the y-direction of the sample body to be isolated are carved out by virtue of corresponding rectangular volumes of the substrate material being carved out in oblique and perpendicular incidence of the laser beam. FIGS. 1B and 1C show the same processing state in orientations rotated by 90° relative to one another. In the perspective of FIG. 1C, it can easily be identified that work was carried out with an oblique incidence of the laser beam at the longitudinal sides (extending parallel to the x-direction) of the sample body to be released to provide a sample body which has the form of an asymmetric prism. A first side face or flank face S1 extends perpendicular to the substrate surface. The opposite plane second side face S2 extends obliquely with respect to the substrate surface in the style of an undercut. The two side faces S1 and S2 in plane intersect at a distance below the substrate surface in the interior of the substrate at a depth only corresponding to a fraction of the substrate thickness measured perpendicular to the substrate surface. Thus, the sample body can also be isolated from a region close to the surface without it being necessary for the substrate to be separated over the whole thickness.

The situation shown in FIG. 1C represents an intermediate stage of the processing in which the sample body has not yet obtained its subsequent design provided for the removal. Subsequently, the sample body is thinned further in the y-direction in a central portion between the outer holding structures by virtue of laser beam processing with virtually perpendicular beam incidence being used to remove substrate material such that the dumbbell form of the sample body shown in FIG. 1D, which is also depicted in FIG. 2, arises. The sample body PK now has a first handling portion HA1 adjacent to the first holding structure HS1, a second handling portion HA2 adjacent to the opposite second holding structure HS2 and, between the handling portions, a target portion ZA, which is thinner in comparison and in which the target volume ZV lies. The sample body top side PO appearing C-shaped in this plan view is formed by a correspondingly formed portion of the substrate surface SO.

The plane first side face S1 is perpendicular to the sample body top side and extends in the z-direction of the substrate. The opposite side face S3 extends parallel to the first side face S1 such that the target portion ZA has the form of a plane parallel plate. By cutting away the central portion to generate the side face S3, rectangular interior angles IW arose at the transition between the target portion ZA and the adjoining handling portions. The plane side faces abutting against one another in the region of the interior angles subsequently act as abutment faces during the positionally correct fixation of the sample body at the associated sample body holder, which abutment surfaces enable precise positioning in x- and y-direction; cf. FIG. 3.

The schematic FIG. 2 shows a view of a sample body PK with a comparable geometry isolated from a substrate containing two thin layers L1, L2 in the region of the substrate top side on a volume material, with the thin layers being separated by an interface G1 parallel to the surface. It is possible to identify that the thin target portion ZA is aligned perpendicular to the former substrate surface such that an examination of the interface G1 and the adjoining layers L1, L2 is possible in an observation direction BR extending substantially parallel to the interface G1 and the adjoining layers (arrow), in a sufficient reduction in the thickness of the target portion measured parallel to the substrate top side in the y-direction. Therefore, a cross-sectional preparation is readily possible by the method.

As already mentioned above, the target portion can already be thinned to a very thin overall thickness D when the sample body is still held in the substrate before the sample body is detached from the substrate.

The following typical dimensions of handling portion and target portion were found to be particularly practical. Deviations are possible. The target portion should be as thin as possible so that the subsequent processing steps require as little time as possible. Overall thicknesses D down to approximately 40 µm appear possible on a regular basis. The minimum thickness can vary depending on the material. The thickness of the handling portions as measured in the same direction (y-direction) is usually many times larger and can likewise be controlled in a material-dependent manner. It depends, inter alia, on the strength of the substrate material. For silicon and other semiconductor materials, a handling portion should be e.g. at least 200 µm thick, the thickness or length in the x-direction being able to have the same order of magnitude. For materials with greater strength such as sapphire ($Al_2O_3$), thicknesses of 100 µm to 150 µm in the y-direction may be sufficient.

Figure 3:
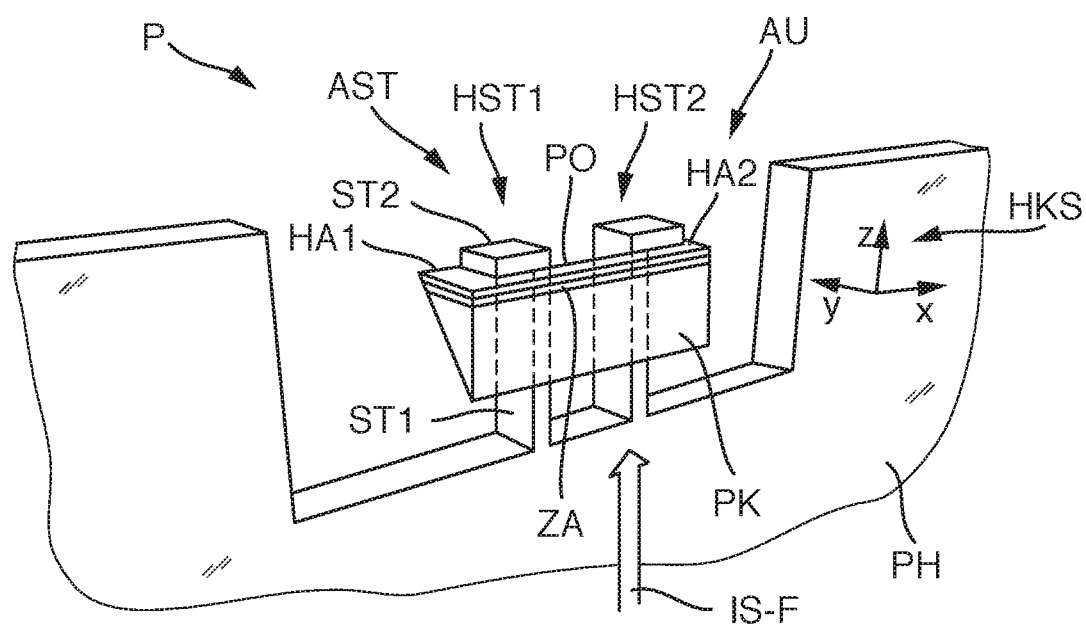
FIG. 3 shows the sample body from FIG. 2 after affixing the sample body to a sample body holder adapted thereto.

In the example, the sample body PK with the not yet completely thinned target portion is removed from the substrate and affixed in a defined accommodation position at a sample body holder PH specially adapted to the sample body geometry (cf. FIG. 3).

Figure 5:
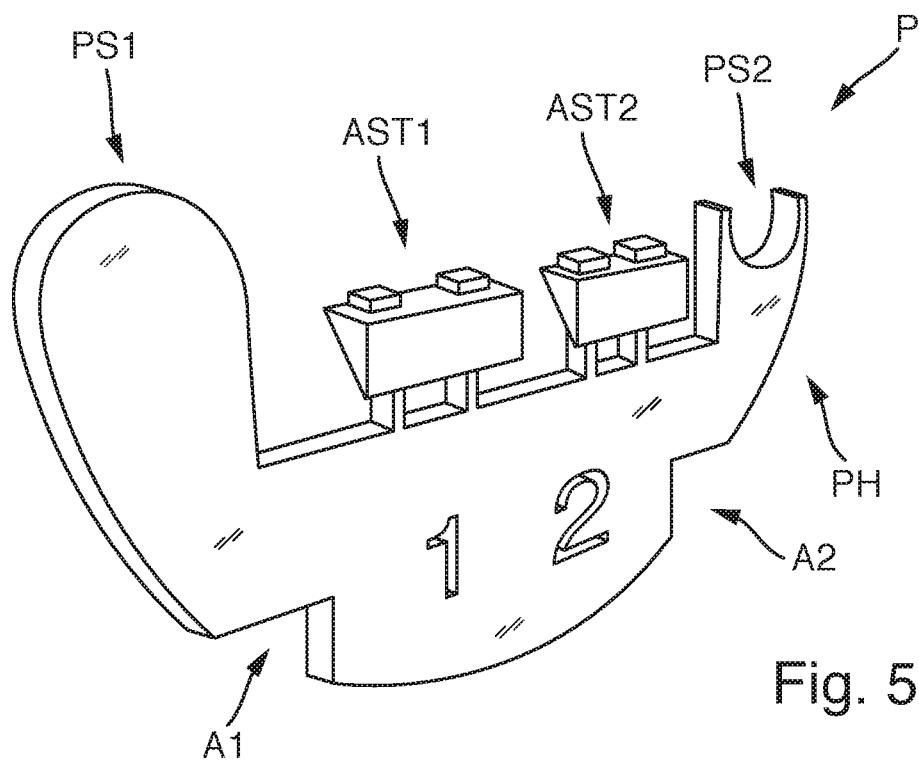
FIG. 5 shows an example of a sample body holder with two identically designed accommodation structures for accommodating two sample bodies.

The sample body holder PH of the example is an integral, flat functional element prepared by laser processing from a thin film of a metallic material (e.g. titanium) in a manner fitting to the geometry of the sample body. The generally plate-shaped sample body holder PH approximately has the basic shape of a semicircle (cf. FIG. 5), at the circle-halving side of which a rectangular recess AU (or recess with a different design) is formed. On the opposite arcuate side, two triangular recesses A1, A2 are provided lying opposite one another, the recesses being delimited by two edges aligned perpendicular to one another. This geometry simplifies the positionally correct attachment of the sample body holder or of the entire sample in a clamp mounting (not described in any more detail here), which can be used for further processing steps. In this respect, the geometry of the sample holder is similar to the geometry of samples which is described in EP 2 787 338 A1 together with the function of these recesses. In this respect, reference is made to the description therein.

Accommodation structures AST have been carved out centrally in the region of the recess AU at the top side, which accommodation structures render it possible to accommodate the sample body PK adapted thereto in terms of structure, in an accommodation position precisely defined in terms of the holder coordinate system HKS on the sample body holder. The accommodation structures AST may comprise two holding webs HST1, HST2 to affix the sample body, which holding webs each have an L-shaped design and are arranged mirror symmetrically with respect to a central plane. Each one of the holding webs HST1, HST2 has a first web portion ST1 which 1) is vertical in the shown configuration, 2) protrudes from the solid part and 3) at the free end thereof, supports a shorter second web portion ST2 at right angles thereto, the second web portion projecting outward toward the side facing away from the other holding web. The web portions ST1, ST2 each have a rectangular cross section and form a right angle with respect to one another.

In another example not depicted here, there still is a third web portion parallel to the first web portion, the third web portion adjoining the second web portion at the outside such that the web portions form a rectangular eye or an eye with a rectangular opening.

The lateral distance (in the x-direction) of the outer sides of the vertical first web portions ST1 facing away from one another is smaller by several 10 µm (e.g. at most 50 µm) than the clear distance between the side faces of the handling portions HA1, HA2 facing one another such that the sample body sits on the holding webs with little play in the x-direction after being pushed onto the holding webs in the lateral direction (in the y-direction) and the sample body, with the inner side thereof, is able to abut against the holding webs in the y-direction. The outwardly projecting shorter second web portions ST2 form an abutment surface in the longitudinal direction of the first web portions ST1 (i.e. in the z-direction), against which abutment surface the sample body with the sample body top side PO can abut. Hence, the accommodation position of the sample body is defined in the y-direction and in the vertical direction (z-direction) by stops at the holding webs.

The sample body geometry with the two solid handling portions lying at a lateral distance from one another and an inner face or inner flank perpendicular to the surface is particularly advantageous, albeit not mandatory, since this can be guided in a well-defined manner into the corresponding stops along the two holding webs HST1, HST2 of the sample body holder PH. Prior to attaching the sample body, the portions of the faces of sample body PK and/or holding webs HST1, HST2 to be brought into contact with one another are wetted by an adhesive. The latter is distributed substantially only in the region of tight contact between sample body and holding webs when the sample body is attached such that a very durable, clean adhesive bond can be obtained using minimal amounts of a suitable adhesive.

Both when removing the sample body from the substrate and when affixing the sample body at the holding webs of the accommodation structures of the sample body holder, the mechanically stable handling portions HA1, HA2 allow the sample body to be manipulated with tweezers under observation in a simple stereo light microscope.

No particular requirements are placed on the ambient atmosphere for the complete set of processing steps, including the laser processing, the transfer of the sample body PK from the substrate SUB to the sample body holder PH and the fixation to the sample body holder. However, these steps can be undertaken in normal laboratory atmosphere. In particular, working in a vacuum is not required.

FIG. 3 shows the sample P with a two-part design, which substantially (except for the adhesive material) only consists of the sample body holder PH and the sample body PK affixed thereto. This sample can then be supplied to further processing steps. In particular, after fixation of the sample body at the sample body holder is complete, the sample can be transferred into a special clamp mounting to thereafter precisely thin the target portion ZA to a web thickness (measured in the y-direction) of e.g. approximately 10 µm thickness by laser beam processing from substantially vertically above. Although it is possible in theory to undertake this thinning back when the sample body is still held in the substrate, this thinning back should expediently only take place after fastening the sample body PK to the sample body holder PH as this allows the necessary geometric boundary conditions for the immediate evacuation of processing remains (debris) to be obtained in a particularly simple and reliable manner and as, in the other case, the stability required for the transfer from the substrate to the sample body holder could possibly also be lost.

Use is preferably made of an ultrashort pulse laser for the last phases of the laser processing for the purposes of thinning the target portion ZA and largely exposing the target volume. As result, a sufficient lack of damage can be obtained on the exposed flanks, as result of which only little, and hence time-saving, post-processing by an ion beam becomes necessary. Optionally, it is also possible to use short pulse lasers. In general, the type of laser should be selected such that the damaging thickness is no greater than the material layer to be ablated in any case due to stability.

In the geometry of the sample body and the sample body holder from FIG. 3, which is depicted in an exemplary manner, final post-thinning of the target portion, exposed between the holding webs, down to electron transparency is possible in the region of the target volume with the aid of a focused ion beam IS-F, i.e. by FIB processing. Due to the circumstances that the target portion ZA was already greatly thinned back in the preceding laser processing stages, the advantages of this technology in respect of lack of damage and in respect of target accuracy can be fully employed without having to accept the disadvantages of a processing time that is too long.

Alternatively, post-thinning can also be carried out using a wide ion beam, i.e. a wider, not particularly focused ion beam, e.g. with argon ions or other noble gas ions, which are not very reactive.

As an alternative to adhesive bonding, the two elastically deformable metallic holding webs can be pretensioned in a loading tool such that the sample body can be clamped between the holding webs by splaying the latter. As a result, an adhesive can be dispensed with. An adhesive-free latching hold with partial interlock is also possible in the case of an appropriate design.

To avoid unwanted removal of regions not intended for thinning, shadowing may be advantageous in this case, which shadowing, like in the known procedure in wire shadowing, may lead to a locally precisely defined target volume being able to be exposed despite large-area ion irradiation.

Figure 4:
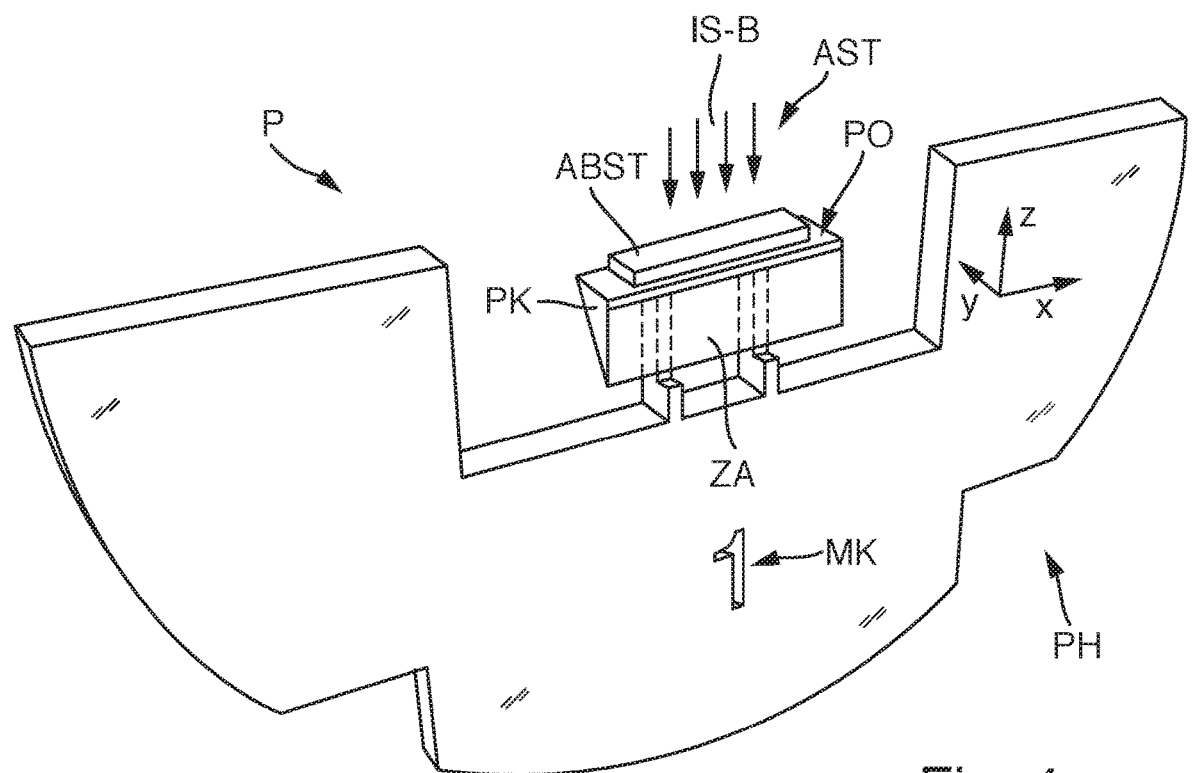
FIG. 4 shows an example of a sample body holder, the accommodation structures of which have a shadowing web adapted to the sample body top side.

FIG. 4 shows an example of a sample body holder PH, the accommodation structures AST of which have a shadowing web ABST adapted to the sample body top side, the shadowing web extending in the x-direction and covering part of the sample body PK sample body top side PO when the sample body is affixed to the holding webs in the region of the plate-shaped target portion ZA. In the sample body holder produced from a titanium film by laser processing, the shadowing web embodied integrally with the remainder of the sample body holder is likewise made of titanium having a substantially lower etching rate under argon ion bombardment compared to the semiconductor material of the sample body PK. The material of the shadowing web protects the volume region of the target portion situated directly therebelow from an attack by ions until the material of the shadowing web is largely used up. The ion beam processing with an unfocused wide ion beam IS-B is then completed if a target volume with a suitably small thickness (in the y-direction) remains under the largely etched-away shadowing web and before this target volume is also etched away by the ions. In this manner, a target preparation of cross-sectional samples with layers close to the surface can be carried out, even when using a wide ion beam, which can be generated in a significantly more cost-effective manner, for post-thinning.

It is possible to modify the cross section of the shadowing web or shadowing bar by laser micro-processing such that a peaked-roof structure, which promotes the process of ion beam thinning, arises. Instead of post-thinning by a focused ion beam, this is then followed only by ion beam processing with a wide beam ion processing machine.

To further increase the throughput, a sample body holder can also have more than one accommodation structure, for example, two identical accommodation structures AST1, AST2 lying next to one another, which each have holding webs like the accommodation structure from FIG. 3 (FIG. 5) to accommodate a sample body.

Figure 6:
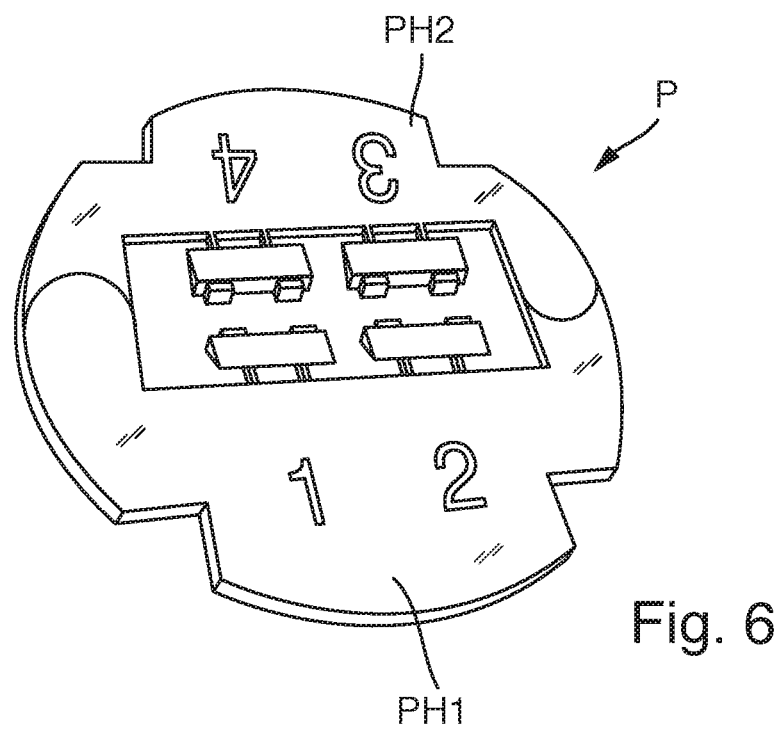
FIG. 6 shows a sample which has two sample body holders adapted to one another, which sample body holders each carry two sample bodies affixed thereto.

Furthermore, pair-wise complementary fitting pieces PS1, PS2 can be worked out at side regions of sample body holders, the fitting pieces rendering it possible to use two sample body holders PH1, PH2, with sample bodies affixed thereon, together as a sample P and to install the latter into a corresponding holder of a microstructure examination installation, e.g. into a standard sample holder of a transmission electron microscope (cf. FIG. 6). In this way, it is possible to increase not only the efficiency of the preparation, but also the efficiency of the subsequent analysis since, inter alia, seal-system times can be reduced or avoided.

Various examples deviating from the examples described above are possible. By way of example, it is not necessary for a handling portion or for both handling portions to be arranged at the edge or at the end of a sample body. In the example in FIG. 7, the sample body PK has two handling portions HA1, HA2 arranged approximately in the central region of the sample body in the longitudinal direction (x-direction) thereof such that a first target portion ZA1 is present on one side of the pair of handling portions and a second target portion ZA2 is present on the opposite side. The thin, plate-shaped target portions therefore lie at the free ends of the sample body, while the holding thereof takes place in the central region.

Figure 7:
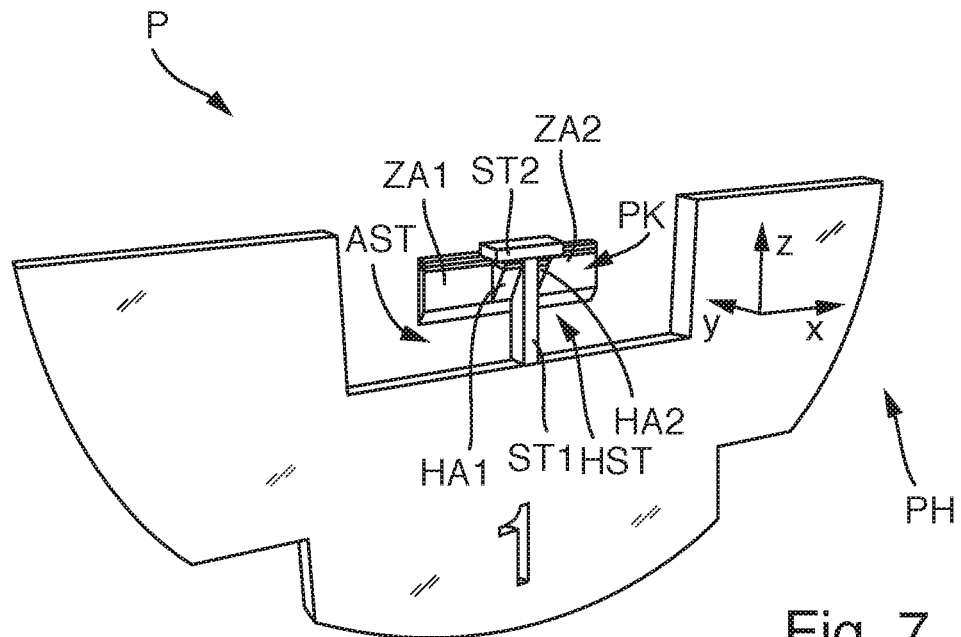
FIG. 7 shows a sample body holder with a T-shaped holding web and a sample body affixed thereon.

The sample body holder PH adapted to this form of the sample body in FIG. 7 has accommodation structures AST formed by a single, T-shaped holding web HST. This has a relatively long web portion ST1 extending in the z-direction, at the free end of which a shorter second web portion ST2 protruding in the longitudinal direction on both sides is formed. The clear distance measured in the x-direction between the two handling portions is slightly greater than the width of the first web portion ST1 measured in this direction such that the sample body can be pushed onto the first web portion ST1 largely without play in the y-direction. An intermediate portion serving as a stop in the y-direction is situated flush with the target portions between the handling portions. The perpendicular web portion ST2 forms an upper stop, effective in the z-direction, for the sample body, against which the latter rests with the sample body top side PO thereof. Like in the other examples, the sample body is fastened to the holding web HST by adhesive bonding.

Figure 8:
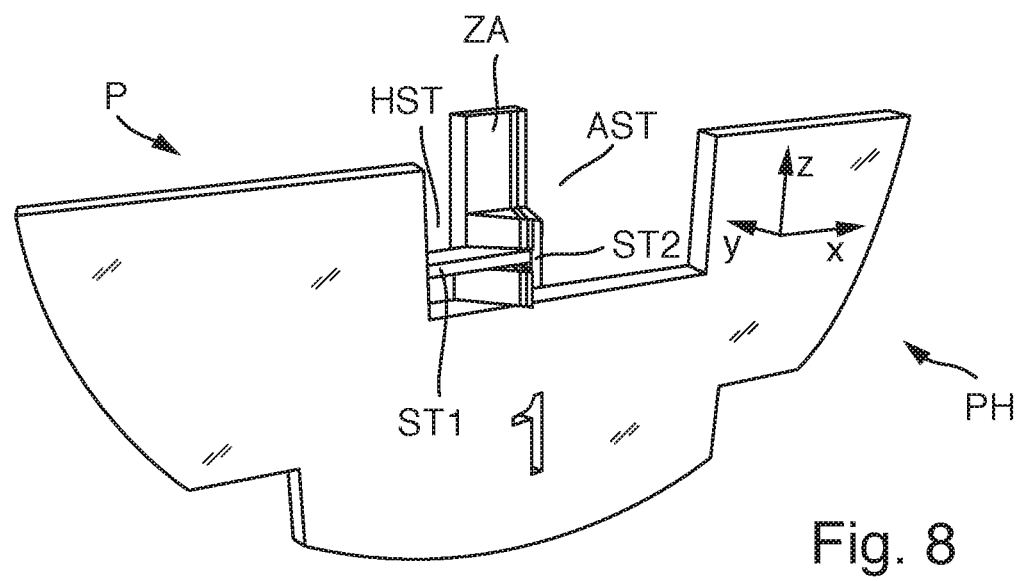
FIG. 8 shows another sample body holder with a T-shaped holding web and an upright sample body affixed thereon.

In the example in FIG. 8, the holding web HST of the accommodation structures AST likewise has a T-form, but the longer first web portion ST1 is aligned in the x-direction (horizontally in FIG. 8), while the crossbar or second web portion ST2 perpendicular thereto is aligned parallel to the z-direction. The sample body PK has two handling portions HA1, HA2 connected by way of an intermediate piece and between which there is an interstice with a width equaling the thickness of the first web portion ST2. Overall, the pair of handling portions is situated in an end region of the sample body, while the target portion ZA extends on one side to the other end region and, in the present case, it is aligned parallel to the z-direction. Such a sample body with an "upright" alignment can serve, for example, for the preparation of a sample for atom-probe tomography (LEAP) or for x-ray tomography/x-ray microscopy.

It is clear that, within the scope of examples herein, the last step of ion beam thinning can be carried out both by any type of focused ion beam processing (Ga-ions/plasma-FIB) and by wide beam ion etching.

As shown in e.g. FIGS. 4 to 8, markings MK in the form of digits or the like can be introduced into the sample body holder, for example, for improved tracking. This is easily possible by a laser beam.

Some aspects of our methods and samples have been explained using the example of samples for transmission electron microscopy. However, the use of the methods is not restricted thereto. Samples for numerous other microstructure diagnostic methods can likewise be prepared according to the described method or examples thereof.

By way of example, use is made of methods of imaging using x-rays, which, outside of synchrotron radiation sources, were pure tomographic shadow-casting methods (x-ray computed tomography) for a long time and which were developed in recent years to x-ray microscopy. In the latter method (x-ray microscopy, XRM), there is a two-stage magnification. Post magnification follows the shadow-casting principle. Due to the penetration capability of x-ray radiation and due to the circumstances that the sample needs to be rotated between x-ray source and detector for the high-resolution examination of the 3D structure, a requirement of XRM samples is that they have a small diameter (typical: a few to several 10 µm). A preparation by laser micro-processing is likewise well suited to this end.

The invention claimed is:

1. A method of preparing a sample for microstructure diagnostics, wherein a sample body with a predeterminable form is prepared from a substrate by way of material-ablating laser beam processing and subsequently a target portion of the sample body is further processed by laser beam processing and/or ion beam processing to expose a target volume suitable for a microstructure examination, comprising:
  (a) releasing the sample body from the substrate by at least one laser processing operation by radiating-in at least one laser beam in a manner perpendicular and/or oblique to a substrate surface such that a sample body arises, said sample body being delimited at a sample body top side by a region of the substrate surface and, laterally, by side faces oriented in an oblique or perpendicular manner in relation to the substrate surface, wherein a form of the sample body is generated, which form has at least one solid handling portion and, adjoining the handling portion, a target portion thinner relative to the handling portion, said target portion being delimited at a narrow side by the sample body top side and, laterally, by side faces extending in a perpendicular or oblique manner in relation to the sample body top side;
  (b) producing a sample body holder separate from the sample body and having accommodation structures adapted to the form of the sample body for the purposes of accommodating the sample body in a defined accommodation position;
  (c) removing the sample body that was released from the substrate;
  (d) affixing the sample body removed from the substrate directly to the accommodation structures of the sample body holder;
  (e) carrying out at least one further material-ablating processing step of at least one side face of the sample body in the region of the target portion by laser beam processing and/or ion beam processing to expose the target volume.

2. The method according to claim 1, wherein, in the region of the substrate surface, the substrate has one or more layers or layer segments separated by interfaces, the sample body being generated such that one or more interfaces are oriented substantially perpendicular to at least one side face of the target portion.

3. The method according to claim 1, wherein the sample body is designed such that an interior angle arises between the target portion and an adjoining handling portion, with a side face of the target portion and a side face of the handling portion intersecting at an angle at said interior angle.

4. The method according to claim 1, wherein the sample body holder is manufactured from a holder material different from the substrate material, with the holder material having a metal or being a metal, and/or with the sample body holder being produced by laser processing from a plate or a film of the holder material.

5. The method according to claim 1, wherein a defined area contact is generated at two faces at an angle in relation to one another when affixing the sample body to the sample body holder such that the position of the sample body in respect of the sample body holder is set in at least two mutually perpendicular directions.

6. A method of preparing a sample for microstructure diagnostics, wherein a sample body with a predeterminable form is prepared from a substrate by way of material-ablating laser beam processing and subsequently a target portion of the sample body is further processed by laser beam processing and/or ion beam processing to expose a target volume suitable for a microstructure examination, comprising:
  (a) releasing the sample body from the substrate by at least one laser processing operation by radiating-in at least one laser beam in a manner perpendicular and/or oblique to a substrate surface such that a sample body arises, said sample body being delimited at a sample body top side by a region of the substrate surface and, laterally, by side faces oriented in an oblique or perpendicular manner in relation to the substrate surface,
wherein 1) a form of the sample body is generated, which form has at least one solid handling portion and, adjoining the handling portion, a target portion thinner relative to the handling portion, said target portion being delimited at a narrow side by the sample body top side and, laterally, by side faces extending in a perpendicular or oblique manner in relation to the sample body top side, and 2) the sample body is designed such that an interior angle arises between the target portion and an adjoining handling portion, with a side face of the target portion and a side face of the handling portion intersecting at an angle at the interior angle;

(b) producing a sample body holder separate from the sample body and having accommodation structures adapted to the form of the sample body for the purposes of accommodating the sample body in a defined accommodation position;

(c) removing the sample body that was released from the substrate;

(d) affixing the sample body removed from the substrate directly to the accommodation structures of the sample body holder, wherein a defined area contact is generated at two faces at an angle in relation to one another at the interior angle such that the position of the sample body in respect of the sample body holder is set in at least two mutually perpendicular directions;

(e) carrying out at least one further material-ablating processing step of at least one side face of the sample body in the region of the target portion by laser beam processing and/or ion beam processing to expose the target volume.

7. The method according to claim 6, wherein the sample body is fastened to the accommodation structures by adhesive bonding or clamping.

8. The method according to claim 6, wherein a first handling portion and a second handling portion are generated, and a thin intermediate portion lies between the first handling portion and the second handling portion, the intermediate portion being configured as target portion.

9. The method according to claim 6, wherein the accommodation structures have one or more holding webs to affix the sample body, and at least one of the conditions is satisfied:
(i) at least one abutment face to mount a corresponding side face of the sample body is on a holding web, with an exterior angle formed at a holding web and adapted to the interior angle formed on the sample body between the target portion and an adjoining handling portion;
(ii) the holding web having a first web portion and a second web portion oriented at an angle to the first web portion, with the angle being a right angle and/or a holding web having a T-shape or an L-shape.

10. A sample for microstructure diagnostics comprising;
a sample body holder with accommodation structures to accommodate a sample body in a defined accommodation position; and
at least one sample body produced separately from the sample body holder, said sample body having 1) at least one solid handling portion and, adjoining the handling portion, a target portion thinner relative to the handling portion, said target portion being delimited at a narrow side by a sample body top side and, laterally, by side faces extending in a perpendicular or oblique manner in relation to the sample body top side, and 2) an interior angle that arises between the target portion and an adjoining handling portion, with a side face of the target portion and a side face of the handling portion intersecting at an angle at the interior angle;
with the sample body being affixed directly to the accommodation structures in the accommodation position, wherein a defined area contact is generated at two faces at an angle in relation to one another at the interior angle such that the position of the sample body in respect of the sample body holder is set in at least two mutually perpendicular directions.

11. A method of preparing a sample for microstructure diagnostics, wherein a sample body with a predeterminable form is prepared from a substrate by way of material-ablating laser beam processing and subsequently a target portion of the sample body is further processed by laser beam processing and/or ion beam processing to expose a target volume suitable for a microstructure examination, comprising:
(a) releasing the sample body from the substrate by at least one laser processing operation by radiating-in at least one laser beam in a manner perpendicular and/or oblique to a substrate surface such that a sample body arises, said sample body being delimited at a sample body top side by a region of the substrate surface and, laterally, by side faces oriented in an oblique or perpendicular manner in relation to the substrate surface,
wherein a form of the sample body is generated, which form has at least one solid handling portion comprising a thickness of at least 100 µm in in at least direction parallel to the sample body top side and, adjoining the handling portion, a target portion thinner relative to the handling portion, said target portion being delimited at a narrow side by the sample body top side and, laterally, by side faces extending in a perpendicular or oblique manner in relation to the sample body top side;

(b) producing a sample body holder separate front the sample body and having accommodation structures adapted to the form of the sample body for the purposes of accommodating the sample body in a defined accommodation position;

(c) removing the sample body that was released from the substrate with tweezers or other gripper instrument and transferring the sample body to the sample body holder in an ambient atmosphere;

(d) affixing the sample body removed from the substrate directly to the accommodation structures of the sample body holder;

(e) carrying out at least one further material-ablating processing step of at least one side face of the sample body in the region of the target portion by laser beam processing and/or ion beam processing to expose the target volume.

* * * * *